Figure 1A:
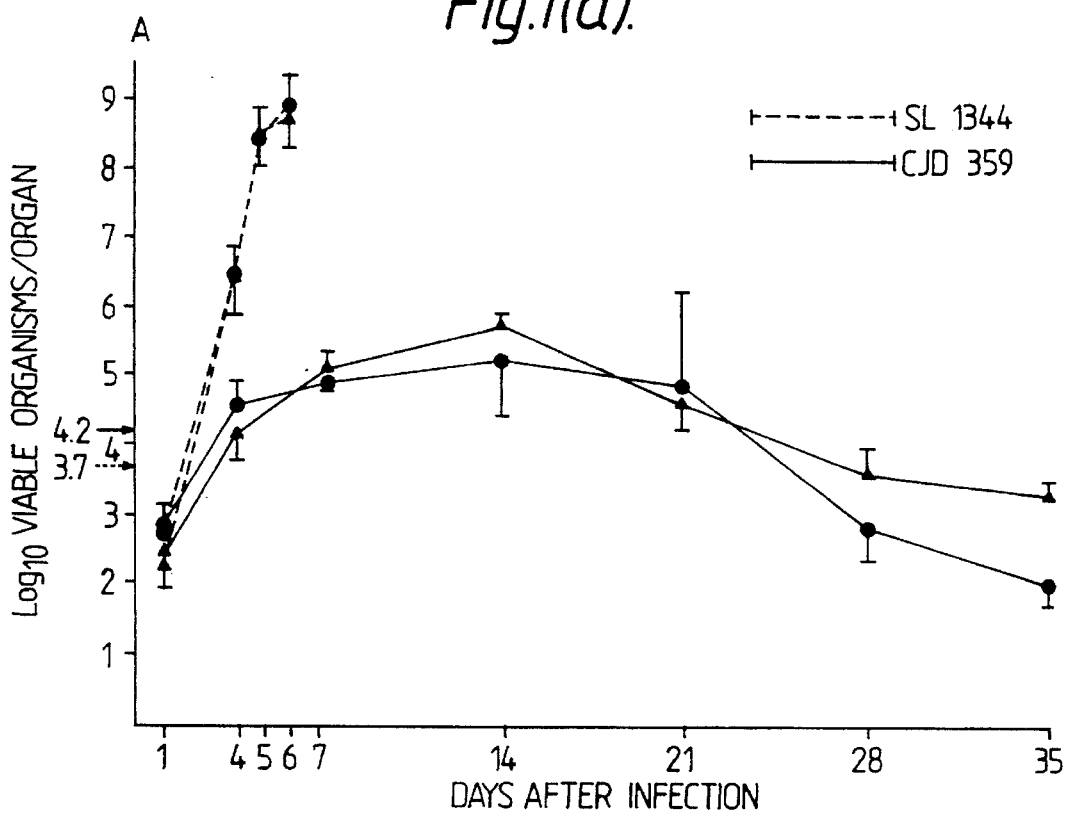

United States Patent [19]
Dougan et al.

[11] Patent Number: 5,527,529
[45] Date of Patent: Jun. 18, 1996

[54] VACCINES COMPRISING ATTENUATED SALMONELLA HAVING MUTATIONS IN THE OMPR GENES

[75] Inventors: Gordan Dougan; Steven N. Chatfield, both of Kent; Christopher F. Higgins, Oxford, all of England; Charles J. Dorman, Dundee, Scotland

[73] Assignees: The Wellcome Foundation Limited; The Royal Society, both of London; The Lister Institute of Preventive Medicine, Middlesex, all of England; The University Court of The University of Dundee, Dundee, Scotland

[21] Appl. No.: 419,741

[22] Filed: Apr. 10, 1995

Related U.S. Application Data

[63] Continuation of Ser. No. 827,584, Jan. 27, 1992, abandoned, which is a continuation of Ser. No. 528,972, May 29, 1990, abandoned.

[30] Foreign Application Priority Data

May 30, 1989 [GB] United Kingdom ................... 8912330

[51] Int. Cl.$^6$ .................. A61K 39/112; C12M 15/74
[52] U.S. Cl. ....................... 424/258.1; 424/93.48; 424/826; 435/69.3; 435/172.1; 435/172.3; 435/252.33; 435/252.8; 435/320.1
[58] Field of Search ................ 424/258.1, 33.48, 424/826; 435/172.1, 172.3, 320.1, 69.3, 252.33, 252.8

[56] References Cited

U.S. PATENT DOCUMENTS 4,837,151  6/1989  Stocker .............................. 435/172.3

FOREIGN PATENT DOCUMENTS

| | | |
|---|---|---|
| 2076287 | 12/1981 | United Kingdom . |
| 0184086 | 6/1986 | United Kingdom . |
| 89/09616 | 10/1989 | WIPO . |
| 90/11687 | 10/1990 | WIPO . |

OTHER PUBLICATIONS

S. Miller et al., Proc. Natl. Acad. Sci. USA, vol. 86:5054–5058 (Jul. 1989).
Curtiss et al., Inf. & Imm., vol. 55:3035–3043 (1987).
Curtiss et al., Vaccine, vol. 6:155–160 (1988).
Fields et al., Science, vol. 243:1059–1062 (Feb. 1989).
V. Miller et al., J. Bact., vol. 170:2575–2583 (1988).
Weiss et al., Inf & Imm. vol. 42:33 (1983).
J. Miller et al., Science, vol. 243:916–922 (1989, Feb.).
Nara et al., Mol. Gen. Genet., vol. 202:194–199 (1986).
Liljestrom et al., J. Bacteriol., vol 169, No. 1, pp. 438–441 (1987).
Nara et al, Mol. Gen. Genet., 205:51–55 (1986).
Chatfield et al., Infection and Immunity, vol. 59, No. 1, 449–452 (1991).
Chatfield et al., Vaccine, vol. 7, 495–498 (1989).
O'Callaghan et al., Infection and Immunity, vol. 56, No. 2, 419–423 (1988).
McFarland et al., Microbial Pathogenesis, 3, 129–141 (1987).
Winans et al, "A gene essential for Agrobacterium virulence is homologous to a family of positive regulatory loci", Proceedings of the National Academy of Sciences of the United States of America 83(21):8278–8282 (1986).
Liljestroem et al, "Cloning of the Regulatory Locus ompB of *Salmonella typhimurium* LT-2. I. Isolation of the ompR Gene and Identification of its Gene Product", Mol. Gen. Genet. 188(2):184–189 (1982).
Liljestroem et al, "Structure and Expression of the ompB Operon. the Regulatory Locus for the Outer Membrane Porin Regulory in *Salmonella typhimurium* LT-2", Journal of Molecular Biology 201(4):663–673 (1988).
Pirhonen et al, "In vivo cloning ad characterization of mutations of the regulatory locus ompR of *Escherichia coli* K 12", Mol. Gen. Genet. 203(3):520–523 (1986).
Dorman et al, "Characterization of Porin and ompR Mutants of a Virulent Strain of *Salmonella typhimurium*: ompR Mutants Are Attenuated In Vivo" Infection and Immunity 57(7):2136–2140 (1989).
Groisman et al, "*Salmonella typhimurium* phoP virulence gene is a transcriptional regulator", Proceedings of the National Academy of Sciences of the United States of America 86(18):7077–7081 (1989).
Ikenaka et al, "A dominant mutation in *Escherichia coli* OmpR lies within a domain which is highly conserved in a large family of bacterial regulatory proteins", Mol. Gen. Genet. 211(3):538–540 (1988).
Bernardini et al, "The two–Component Regulatory System OmpR-EnvZ Controls the Virulence of Shigella flexneri", Journal of Bacteriology 172(11):6274–6481 (1990).
Levine et al, "Attenuated Salmonella Typhi as Live Oral Vaccines to Prevent Typhoid Fever and as Carrier Vaccines to Express Foreign Antigens", Biology of Salmonella, Edited by Cabello et al, Plenum Press, New York, pp. 343–346 (1993).
Puente et al, "Expression of *Salmonella typhi* and *Escherichia coli* OmpC is influenced differently by medium osmolarity; dependence on *Escherichia coli* OmpR", Molecular Microboligy 5(5):1205–1210 (1991).
Fang et al, "The alternative δ factor KatF (RpoS) regulates Salmonella virulence", Proc. Natl. Acad. Sci. USA 89:11978–11982 (1992).

(List continued on next page.)

*Primary Examiner*—John L. LeGuyader
*Attorney, Agent, or Firm*—Nixon & Vanderhye

[57] ABSTRACT

The present invention discloses a novel approach to attenuating bacteria and for their use as live vaccines. The vaccines can be used in human and animal medicine.

In particular, there is disclosed a method of attenuating a bacteria by mutating a gene concerned with the regulation of one or more genes concerned with expression of outer membrane proteins, particularly porin proteins.

8 Claims, 1 Drawing Sheet

OTHER PUBLICATIONS

Hone et al, "Construction of genetically defined double *aro* mutants of *Salmonella typhi*", Vaccine 8:810–816 (1991).

Miller et al, "Bacteriophage P22 as a vehicle for transducing cosmid gene banks between smooth strains of *Salmonella typhimurium*: Use in identifying a role for *aro*D in attenuating virulent Salmonella strains", Mol. Gen. Genet. 215:312–316 (1989).

Dougan et al, "Construction and Characterization of Vaccine Strains of Salmonella Harboring Mutations in Two Different *aro* Genes", The Journal of Infectious Diseases 158(6):1329–1335 (1988).

Miller et al, "Isolation of Orally Attenuated *Salmonella typhimurium* following *TnphoA* Mutagenesis", Infection and Immunity 57(9):2758–2763 (1989).

Collins, "Vaccines and Cell–Mediated Immunity", Bacteriological Reviews 38(4):371–402 (1974).

Jones et al, "Oral vaccination of calves against experimental salmonellosis using a double *aro* mutant of *Salmonella typhimurium*", Vaccine 9:29–33 (1991).

Tacket et al, "Clinical acceptability and immunogenicity of CVD 908 *Salmonella typhi* vaccine strain", Vaccine 10:338–341 (1992).

Tacket et al, "Comparison of the Safety and Immunogenicity of $\Delta aroC$ $\Delta aroD$ and $\Delta cya$ $\Delta crp$ *Salmonella typhi* Strains in Adult Volunteers", Infection and Immunity 60(2):536–541 (1992).

VACCINES COMPRISING ATTENUATED SALMONELLA HAVING MUTATIONS IN THE OMPR GENES

This is a continuation of application Ser. No. 07/827,584, filed Jan. 27, 1992, now abandoned, which was a continuation of application Ser. No. 07/528,972, filed May 29, 1990, now abandoned.

The present invention relates to attenuated microorganisms, to methods for their production, to their use in animal and human medicine and to pharmaceutical compositions containing them.

In 1950 Bacon et al (Br.J.Exp. Path. 31, 714–724) demonstrated that certain auxotrophic mutants of *S.typhi* were attenuated in mice when compared to the parental strain. Certain of these auxotrophic mutants have been proposed as being suitable candidates for the basis of a whole cell vaccine. (See for example Hosieth and Stocker (Nature, 241, 238–39, UK patent application 87/30037, The Wellcome Foundation)).

Together with envZ, ompR forms a two gene operon, previously designated ompB. The nucleotide sequence of this locus is highly conserved between *Escherichia coli* and *Salmonella typhimurium*. The ompR gene is primarily concerned with the regulation of osmotically-responsive genes and acts in concert with envZ. ompR and envZ genes form a single transcription unit with translationally coupled expression (Liljestrom et al., J.Mol.Biol. 201, 663–673 1988). OmpR has been identified as a positive activator of gene expression (Jo et al. J.Bacteriol, 140, 843–847; Norioka et al J.Biol.Chem, 261 15252 1986) while EnvZ has been shown to be associated with the inner membrane (Forst et al., J.Biol. Chem. 262 16433 1987). It has been proposed that EnvZ acts as an environmental sensor and transmits signals to OmpR, modulating the transcriptional control activity of the latter (Hall and Silhavy, J.Mol.Biol. 151 1 1981). A pleiotropic mutation in envZ has been shown to be suppressed by a mutation in ompR, providing genetic evidence that the products of these genes functionally interact (Matsuyama et al., J.Bacteriol 168 1309–1314 1986). Moreover, suppressor mutations of envZ have been mapped to rpoA, the gene coding for the A subunit of RNA polymerase. This suggests that OmpR and RNA polymerase interact (Garrett and Silhavy, J.Bacteriol 169 1379 1987; Matsuyama and Mizushima, J.Mol.Biol. 195 847 1987). The genes which are ompR dependent for transcription are primarily those coding for the major outer membrane porins OmpC and OmpF, although expression of the *S.typhimurium* tppB operon, coding for a tripeptide permease, has been reported to be OmpR-dependent (Gibson et al Mol.Gen. Genet. 297 120–129 1987). Binding sites for OmpR have been biochemically identified upstream of the ompC and ompF promotors (Norioka et al., supra). Expression of these genes is reciprocally regulated by growth medium osmolarity in an OmpR-dependent manner (Aiba et al., J.Bacteriol 169 3007 1987; Kawaji et al., J.Bacteriol 140 843–847 1979; Mizuno, PNAS(USA) 81 1966–70 1987; van Alphen and Lutenberg, J.Bacteriol 131 625–630 1977). In growth media of high osmolarity, the level of OmpC is elevated while that of OmpF is repressed; in media of low osmolarity, the reverse is true.

The present inventors have found that it is possible to attenuate pathogenic bacteria by introducing a mutation into a gene which is concerned with the regulation of one or more other genes. In particular the present inventors have found that pathogenic bacteria may be attenuated by introducing a mutation into a gene concerned with the regulation of genes including those encoding for outer membrane proteins.

Thus, according to the present invention there is provided an attenuated bacterium harbouring a mutation in a gene concerned with the regulation of one or more other genes. Preferably the mutation occurs in the ompR gene or another gene involved in regulation. There are a large number of other genes which are concerned with regulation and are known to respond to environmental stimuli (Ronson et al Cell 49 579–581). Amongst these the following can be mentioned:

The ntrB/ntrC system of *E.coli*, which responds to nitrogen limitation and positively regulates glnA and nifLA (Buck et al., Nature 320 374–378 1986; Hirschman et al., PNAS 82 7525 1985; Nixon et al., PNAS 83 7850–7854 1986, Reitzer and Magasanik, Cell 45 785 1986); the phoR/phoB system of *E.coli* which responds to phosphate limitation (Makino et al., J.Mol.Biol. 192 549–556 1986b); the cpxA/sfrA system of *E.coli* which responds to dyes and other toxic compounds (Albin et al., J.Biol. Chem 261. 4698 1986; Drury et al, J.Biol. Chem 260 4236–4272 1985). An analogous system in Rhizobium is dctB/dctD, which is responsive to 4C-discarboxylic acids (Ronson et al., J.Bacteriol. 169 2424 and Cell 49 579–581 1987). A virulence system of this type has been described in Agrobacterium. This is the virA/virG system, which responds to plant exudates (Le Roux et al., EMBO J. 6 849–856 1987; Stachel and Zambryski., Am.J.Vet.Res. 45 59–66 1986; Winans et al., PNAS US 83 8278 1986).

The attenuated bacteria, according to the present invention, are preferably Gram-negative bacteria which can invade and grow within eucaryotic cells and colonise the mucosal surface. Examples of these include members of the genera Salmonella, Bordetella, Vibrio, Haemophilus, Escherichia. In particular the following species can be particularly mentioned; *S.typhi* the cause of human typhoid; *S.typhimurium*—the cause of salmonellosis in several animal species; *S.enteritidis*—a cause of food poisoning in humans; *S.cholerae-suis*—the cause of salmonellosis in pigs; *Bordetella pertussis*—the cause of whooping cough; *Haemophilus influenzae*—a cause of meningitis; and *Neisseria gonorrhoeae*—the cause of gonorrhoea.

If an attenuated microorganism is to be used in a live form in a vaccine preparation, it is clearly important that such a microorganism does not revert back to the virulent parent. The probability of this happening with a single mutation is considered to be small; however, the risk of reversion occuring in a strain harbouring mutations in two discrete genes, located in different places in the genome, is considered to be insignificant.

The present invention also provides an attenuated bacterium harbouring a first mutation in a regulatory gene and a second mutation in a second gene. Preferably the second gene is a gene encoding for an enzyme involved in an essential biosynthetic pathway, in particular genes involved in the pre-chorismate pathway involved in the biosynthesis of aromatic compounds. The mutations will preferably be in aroA (the gene encoding 5-enolpyruvyl shikimate-3-phosphate synthase), aroC (chorismate synthase) or aroD (3-dehydroquinase).

The attenuated bacteria of the present invention are constructed by the introduction of a stable mutation into the regulatory gene. These mutations may be made by any method known to those skilled in the art. In one embodiment non-reverting mutations were generated by transducing an LT2 ompR::Tn10 marker into *S.typhi* and *S.typhimurium* strains. Tn10 transposon carries a gene encoding for tetracycline resistance. Transductants are selected that are tetracycline resistant by growing colonies on an appropriate medium. Further selection is undertaken by screening for those organisms which have lost the tetracycline resistance gene and which derepressed a tppB::Mud1-8 (lac fusion) under anaerobic growth conditions.

Alternative methods for generating non-reverting mutations include cloning the regulatory gene into a vector eg, a plasmid or cosmid and incorporating a selectable marker gene into the cloned gene, at the same time inactivating that gene. A plasmid carrying the inactivated gene and a different selectable marker can be introduced into the organism by known techniques. It is then possible by suitable selection to identify a mutant wherein the inactivated gene has recombined into the organism's own chromosome and the organism's own copy of the gene has been lost. In particular, the vector used is one which is unstable in the organism (ie. a 'suicide' vector) and will be spontaneously lost. The mutated gene on the plasmid and the organisms own copy of the gene on its chromosome may be exchanged by a genetic crossover event.

Additional methods eliminate the introduction of foreign DNA into vaccine strains at the site of mutations. This can be achieved by cloning the target organism's native gene into a suitable suicide vector (carrying a drug resistance marker) as described above but making a defined deletion in the gene (inactivating it) rather than introducing a selectable marker. This can be introduced into the target organism and the initial selection is made for a single crossover (ie. the organism is drug resistant). Subsequent growth of the strain in the absence of antibiotic and screening of several thousand colonies allows identification of drug sensitive organisms. This may occur in two ways: i) the vector harbouring the deleted gene is lost, ie. the organism is wild type and ii) a second recombination event (resulting in a double crossover) has occured resulting in the replacement of the wild type gene with the deleted gene. We have developed a novel method for screening for the presence of the deletion using the polymerase chain reaction (PCR). Oligonucleotides are synthesised corresponding to regions either side of the deleted region and are used as primers for PCR to amplify the deleted regions from drug sensitive colonies. The amplified product can be analysed by agarose gel electrophoresis. It is possible to distinguish strains harbouring a deleted region as the PCR product is smaller for the deleted gene than for the wild type gene. The PCR product can also be directly sequenced allowing the deletions to be completely defined.

The strains of the present invention may be genetically engineered so as to express antigens from one or more different pathogens. Such pathogens, maybe viral, bacterial, protozoal or of higher parasitic organisms. The pathogens may infect both humans and other mammals, but maybe species selective, or even species specific. Such strains could then form the basis of a bi or multivalent vaccine. Examples of useful antigens include *E. coli* heat labile toxin B subunit (LT-B) *E. coli* K88 antigens, FMDV (Foot and Mouth) peptides, Influenza viral proteins, 69Kd protein from *B.pertussis*, C fragment from tetanus toxin, *C.tetani*. Other antigens which could be usefully expressed would be those from Chlamydia, flukes, mycoplasma, roundworms, tapeworms, rabies virus and rotavirus.

These antigens may be produced by the introduction of the gene or genes encoding them into expression cassettes. Expression cassettes will include DNA sequences, in addition to that coding for the structural gene, which will encode for transcriptional and translational initiation and termination regions. The expression cassette may also include regulatory regions. Such expression cassettes are well known in the art and it is well within the skill of the skilled man to construct them. The expression cassette may be a construct or a naturally occuring plasmid. An example of a genetically engineered attenuated Salmonella which expresses a foreign antigen can be found in EP application No. 0 127 153 A (SSVI/Wellcome). The expression cassette may also be engineered to allow the incorporation of the heterologous gene into the bacterial chromosome, making use of the suicide vector and PCR techniques as previously described and introducing the DNA encoding for foreign antigen into a suitable gene such as ompR, aroA, C or D.

A further bivalent vaccine comprising an attenuated *Salmonella typhi*, capable of expressing the *E.coli* heat-labile enterotoxin subunit B was disclosed by Clements et al (Infection and Immunity, 46, No.2., Nov 1984, p564–569). Ty21a has been used to express other antigens such as the *Shigella sonnet* form I antigen (Formal et al, Infection and Immunity 34 746–750).

According to a second aspect of the invention there is provided an attenuated bacterium, as herein described, transformed with an expression cassette encoding an antigen of a pathogen, wherein in use said antigen is expressed by said attenuated bacterium.

According to a third aspect of the invention we provide a pharmaceutical composition which comprises attenuated bacteria as herein described in admixture with a pharmaceutically acceptable carrier. Preferably the pharmaceutical composition is a vaccine composition.

The vaccine is advantageously presented in a lyophilised form, for example in a capsular form, for oral administration to a patient. Such capsules may be provided with an enteric coating comprising for example Eudragate "S" Eudragate "L" Cellulose acetate, cellulose pthalate or hydroxy propylmethyl cellulose. These capsules may be used as such, or alternatively, the lyophilised material may be reconstituted prior to administration, e.g. as a suspension. Reconstitution is advantageously effected in a buffer at a suitable pH to ensure the viability of the organisms. In order to protect the attenuated bacteria and the vaccine from gastric acidity, a sodium bicarbonate preparation is advantageously administered before each administration of the vaccine. Alternatively the vaccine may be prepared for parenteral administration, intranasal administration or intramammary.

The present invention also provides a method for the prophylactic treatment of a bacterial infection which comprises administering to a patient an effective dose of the above described vaccine. The dosage employed in such a method of treatment will be dependent on various clinical factors, including the size and weight of the patient, the type of vaccine formulated. However, for attenuated *S. typhi* a dosage comprising the administration of $10^9$ to $10^{11}$ *S. typhi* organisms per dose is generally convenient for a 70 kg adult human patient.

In the following, examples are provided of experimental details in accordance with the present invention. It will be understood that these examples are not intended to limit the invention in any way.

EXAMPLE 1

Construction of OmpR mutants in *S.typhimurium*, *S.dublin*

An OmPR deletion was introduced into *S.typhimurium* SL1344, and *S.dublin* using phage P22 (available from Dr. T. Foster, Trinity College, Dublin) transduction. A phage lysate prepared on strain C3D359 was used to transduce all the Salmonella strains, selecting for tetracycline-resistant colonies. Strain CJD359 carries Tn10 inserted in the ompR gene. In order to ensure that the strains were of the OmpR phenotype, P22 lysates were prepared on each strain and used to transduce strain CH776 (available from Prof. C. F. Higgins, ICRF Laboratories, Institute of Molecular Medicine. John Radcliffe Hospital, Oxford, OX3 9DU) which carries a tppB::Mud1-8 (lac) fusion. The strain was checked for derepression of the fusion under anaerobic growth conditions after transduction with the P22 lysates. One isolate from each strain was used to prepare tetracycline-sensitive derivatives by selection on Bochner medium. Several of these were purified and checked for the ompR deletion using PeR technique described above.

An *S.typhimurium* ompR⁻(BRD 578) strain has been deposited at National Collection of Type Cultures, 61 Colindale Avenue, London, NW9 5HT, UK under No. NCTC 12396 on 25th May 1990. An *S.dublin* (BRD 579) ompR⁻ strain has been deposited at National Collection of Type Cultures, 61 Colindale Avenue, London, NW9 5HT, UK under No. NCTC 12398 on 25th May 1990.

EXAMPLE 2

Construction of aroA OmpR mutants in *S.typhimuriuum*, and *S.dublin*

An aroA deletion was introduced into *S.typhimurium* SL1344, and *S.dublin* using the method of McFarland and Stocker. A phase lysate prepared from strainTT472 (available from Dr. B.A.D. Stocker. Stanford University, Calif.) was used to transduce all the Salmonella strains, selecting for tetracycline-resistant colonies. Strain TT472 carries Tn10 inserted within serG which is upstream of and within the same operon as aroA. Tetracycline-resistant transductants were aromatic compound, serine and pyridoxine dependent. A second P22 lysate was prepared, grown on SL5254, (available from Dr. B.A.D. Stocker, Stanford University, Calif.) which has a known deletion within aroA. This was used to transduce the tetracycline resistant strains which were serC:: Tn10 and transductants were selected on minimal median lacking serine and pyridoxine but containing aromatic compounds but in the absence of serine and pyridoxine were tetracycline-sensitive and aromatic compound dependent.

An OmpR deletion was then introduced into all the strains using the method described in example 1.

An *S.typhimurium* (BRD 731) ompR⁻ aroA⁻ strain has been deposited at National Collection of Type Cultures, 61 Colindale Avenue, London, NW9 5HT, UK under No. NCTC 12397 on 25th May 1990. An *S.dublin* (BRD 582) ompR⁻ aroA⁻ strain has Been deposited at National Collection of Type Cultures, 61 Colindale Avenue, London. NW9 5HT. UK under No. NCTC 12399 on 25th May 1990.

EXAMPLE 3

Construction of *Salmonella typhi* OmpR mutant

An ompR deletion was introduced into *S. typhi* as described in example 1. In order to ensure that the strain was of the OmpR phenotype a P22 lysate was prepared on strain CH776 which carries a tppB::Mud1-8 (lac fusion), and transduced into the *S.typhi* strain. The strain was then tested for derepression of the fusion under anaerobic growth conditions.

EXAMPLE 4

Construction of *S.typhi* aroA ompR mutant

*S.typhi* Ty2 aroA was prepared as follows: A cosmid bank of *S.typhi* was constructed into λ phage, and used to transduce a well characterised aroA mutant of *E.coli*. This facilitated the isolation of an aroA clone of *S.typhi*. Subsequent mapping and sequence analysis allowed the identification of convenient restruction sites which were used to construct a defined deletion. The aroA gene harbouring the deletion was introduced into the suicide vector gP704 and a method developed for electroplating into *S.typhi*. The drug resistant colonies were grown in the absence of antibiotics and drug sensitive variants isolated. These were screened for their dependence an aromatic compounds for growth in vitro. A colony that was dependent on these compounds for growth was analysed using Southern hybridisation and PCR confirming the deletion in aroA and absence of any vector DNA. An 9mpR deletion was introduced into this strain as described in Example 3.

*S.typhi* (BRD 732) ompR aroA was deposited at National Collection of Type Cultures, 61 Colindale Avenue, London, UK, under Accession no. NCTC 12395 on 25th May 1990.

EXAMPLE 5

Comparison of attentuation *Salmonella typhimurium* CJD 359 (ompR) with virulent parent strain, *Salmonella typhimurium* SL 1344

The CJD359 strain (now BRD 578) was constructed using transposon-linked mutations into *S.typhimurium* SL1344 using bacteriophage P22-mediated transduction, as described in Example 1.

Infection of mice and enumeration of bacteria in murine organs

BALB/c males of 8–10 weeks of age were used throughout, bred in the animal unit at Wellcome Research Laboratories from breeders originally purchased for OLAC (1976) UK Ltd (Black, Bicester, Oxfordshire, UK). Livers, spleens, mesenteric lymph nodes and Peyer's patches were homogenised as previously described, Mashell et al 1987 Microb. Pathogen, 3, 129–141. Viable counts were performed on these homogenates using L-agar as growth medium. Counts are shown in the figures as geometric means 1 standard errors (n=4 mice per point). For oral inoculation into mice bacteria were grown statically at 37° overnight in 2 liters of L-broth. The culture was centrifuged and the bacterial pellet was resuspended in its own volume and diluted in phosphate buffered salines (pH 7.2) as required. Bacteria in 0.2 ml were administered in 0.2 ml volumes orally to lightly anaethetised mice by gavage needle. The inoculum was calculated by plating appropriate dilutions on L-agar pour plates. For intravenous (iv.) inoculation, mice were injected with 0.2 ml of bacterial suspension into the tail vein. Deaths were recorded over the following four weeks and the $LD_{50}$ was calculated by the method of Reed and Muench 1938 Am.J.Hyg, 27,493–497.

After oral administration CJD359 had an $LD_{50}$ of greater 9.64 log units as compared to the parental strain, SL 1344, which has an $LD_{50}$ of 6.38 log units. (All $LD_{50}$ were calculated after 28 days). Thus CJD359 is highly attenuated. After iv. administration CJD359 had an iv. $LD_{50}$ of Log 5.13 compared to < Log 10 for SL1344 and we again conclude that CJD359 is highly attenuated compared to SL1344.

Figure 1B:
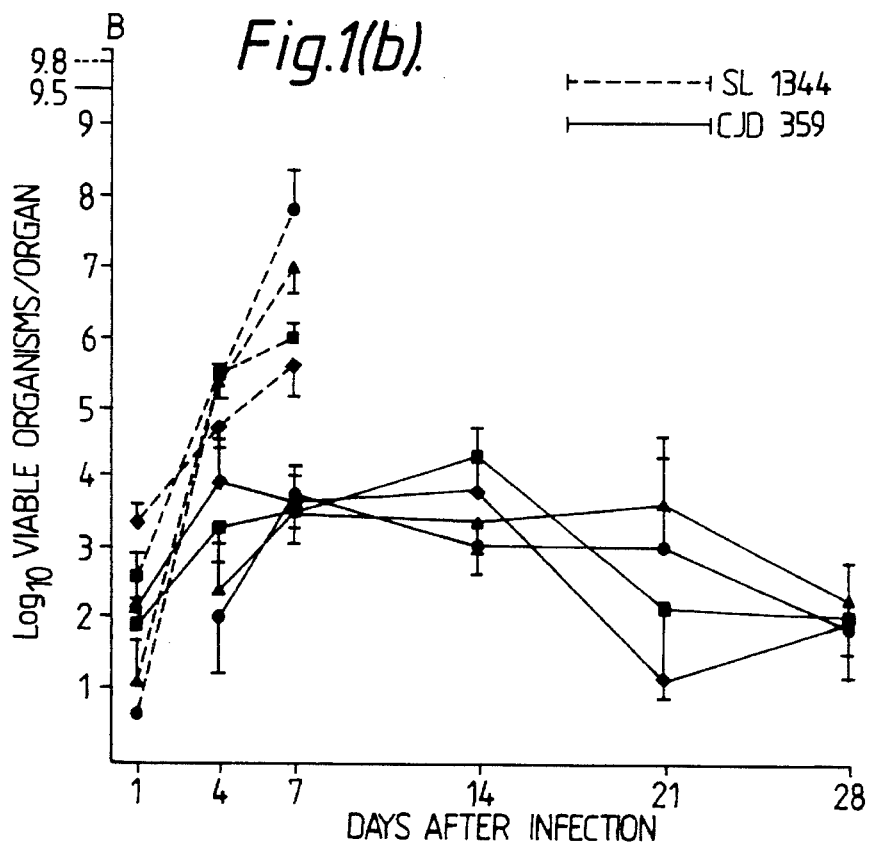

In vivo growth pattern of CJD359 after oral and iv administration to BALB/c mice The ability of SL13444 and CJD359 to grow in vivo after oral or iv administration was assessed. For the iv experiment the numbers of viable organisms in the livers and spleens at different days after challenge were assessed (FIG. 1a). After iv administration of Log 3.7 SL1344 the strain grew rapidly in livers and spleen and all mice died within seven days of challenge. After administration iv of Log 4.2 CJD359 a level of about 10% of the inoculum was detected in the livers and spleens 24 hours later. After this initial drop CJD359 appeared to grow slowly reaching a maximal level of about Log 5 organisms by day 14 and was then slowly cleared. All mice challenged iv with CJD359 exhibited a pronounced splenomegaly during the early phases of the infection. Log 9.8 SL1344 and Log 9.5 CJD359 organisms were administered orally to BALB/c mice and the levels of organisms were assessed in livers, spleens, peyers patches and mesenteric lymph nodes at different times after challenge. Again CJD359 exhibited an impaired ability to grow in vivo compared to SL1344 (FIG. 1b). SL1344 invaded the tissues of all mice challenged and grew rapidly until all mice had died within 14 days of challenge. CJD359 was also able to invade and organisms were detected in peyers patches and mesenteric lymph nodes by day 1 post challenge. By day 4 bacteria had reached liver and spleen and attained a maximal level of colonisation of the host tissue around day 7. Thereafter CJD359 was slowly cleared from the tissues.

Protection of mice after oral challenge

Mice were immunised with Log $10^{10}$ CJD359 and challenged 28 days later with the virulent parental strain SL1344. Mice vaccinated with CJD359 showed excellent protection against challenge with SL1344. The $LD_{50}$ in immunised animals was >Log 9.64 compared with Log 5.64 for unimmunised controls. Thus mice vaccinated orally with CJD359 were well protected against virulent SL1344 challenge.

EXAMPLE 6

Formulation

An attenuated bacterium of the present invention is preferably presented in oral tablet form.

| Ingredient | mg/tablet |
| --- | --- |
| Core-tablets | |
| 1) Freeze-dried excipient carrier containing $10^9$–$10^{10}$ attenuated bacteria | 70.0 |
| 2) Silica dioxide (Aerosil 200) | 0.5 |
| 3) Dipac (97% sucrose) | 235.0 |
| 4) Cross-linked Povidone (Kollidon CL) | 7.0 |
| 5) Microcrystalline Cellulose (Avicel pH 102) | 35.0 |
| 6. Magnesium Stearate | 2.5 |
| | 350.0 |

| Ingredient | mg/tablet |
| --- | --- |
| Coating | |
| 7) Opadry Enteric, OY-P-7156 (Polyvinyl acetate phthalate + Diethylphthate) | 35.0 |
| | 385.0 |

A carrier containing 5% sucrose 1% sodium glutamate and 1% bacto casitone in an aqueous solvent is prepared. The organisms are suspended in this carrier and then subjected to freeze-drying.

The freeze-dried material is blended with Aerosil 200 and the blended mixture is sifted through a screen. The sifted powder is mixed with Dipac, Kollidan CL, Aricel pH 102 and Magnesium Stearate in a blender. This blend is compressed into tablets for subsequent enteric coatings.

The skilled man will appreciate that many of the ingredients in this formulation could be replaced by functionally equivalent pharmaceutically acceptable excipients.

We claim:

1. A pharmaceutical composition for oral administration to a subject for inducing immunity to a pathogenic Salmonella bacterium, which composition comprises a pharmaceutically acceptable excipient and an attenuation form of said Salmonella bacterium, the attenuation being attributable to a non-reverting mutation in the ompR gene of said Salmonella bacterium.

2. A pharmaceutical composition according to claim 1 wherein the attenuated bacterium is selected from the group consisting of *Salmonella typhi*, *Salmonella typhimurium*, and *Salmonella enteriditis*.

3. A pharmaceutical composition according to claim 1 wherein the attenuated Salmonella bacterium additionally harbours a second mutation in a second gene.

4. A pharmaceutical composition according to claim 3 wherein the second mutation is an auxotrophic mutation.

5. A pharmaceutical composition according to claim 4 wherein the second mutation is in a gene encoding an enzyme in an aromatic pathway.

6. A pharmaceutical composition according to claim 5 wherein the second mutation is in a gene selected from the group consisting of aroA, aroC and aroE.

7. A pharmaceutical composition according to claim 1 wherein the attenuated bacterium is selected from the group consisting of *Salmonella typhi* ompR⁻, *Salmonella typhimurium* ompR⁻, *Salmonella dublin* ompR⁻, *Salmonella typhi* aroA⁻ ompR⁻, *Salmonella typhimurium* aroA⁻ ompR⁻, and *Salmonella dublin* aroA⁻ ompR⁻.

8. A pharmaceutical composition according to claim 1 wherein the attenuated Salmonella bacterium is transformed with an expression cassette comprising a gene encoding an antigen from a heterologous pathogen.

* * * * *

UNITED STATES PATENT AND TRADEMARK OFFICE
CERTIFICATE OF CORRECTION

PATENT NO. : 5,527,529
DATED : June 18, 1996
INVENTOR(S) : DOUGAN, et al

It is certified that error appears in the above-indentified patent and that said Letters Patent is hereby corrected as shown below:

On the title page, change item [73] Assignees: from

"The Wellcome Foundation Limited; The Royal Society, both of London; The Lister Institute of Preventive Medicine, Middlesex, all of England; The University Court of The University of Dundee, Dundee, Scotland"

to

--Glaxo Wellcome Inc.; The Royal Society, both of London; The Lister Institute of Preventive Medicine, Middlesex, all of England; The University Court of The University of Dundee, Dundee, Scotland--

Signed and Sealed this

First Day of April, 1997

Attest:

BRUCE LEHMAN

*Attesting Officer*   *Commissioner of Patents and Trademarks*